(12) United States Patent
Dessing

(10) Patent No.: US 11,917,979 B2
(45) Date of Patent: Mar. 5, 2024

(54) MILKING SYSTEM WITH DETECTION SYSTEM

(71) Applicant: LELY PATENT N.V., Maassluis (NL)

(72) Inventor: Jacobus Petrus Maria Dessing, Maassluis (NL)

(73) Assignee: LELY PATENT N.V., Maassluis (NL)

(*) Notice: Subject to any disclaimer, the term of this patent is extended or adjusted under 35 U.S.C. 154(b) by 547 days.

(21) Appl. No.: 17/273,943

(22) PCT Filed: Sep. 19, 2019

(86) PCT No.: PCT/NL2019/050621
§ 371 (c)(1),
(2) Date: Mar. 5, 2021

(87) PCT Pub. No.: WO2020/067883
PCT Pub. Date: Apr. 2, 2020

(65) Prior Publication Data
US 2021/0329877 A1 Oct. 28, 2021

(30) Foreign Application Priority Data
Sep. 24, 2018 (NL) .................................. 2021685

(51) Int. Cl.
*A01J 5/013* (2006.01)
(52) U.S. Cl.
CPC ........... *A01J 5/0135* (2013.01); *A01J 5/0131* (2013.01)
(58) Field of Classification Search
CPC ........ A01J 5/0131; A01J 5/0135; A01J 5/007; G01N 15/0612; G01N 2015/0065; G01N 33/04; Y02E 30/30
See application file for complete search history.

(56) References Cited

U.S. PATENT DOCUMENTS

| 5,096,828 A | 3/1992 | Ishizaka et al. |
| 2002/0124803 A1* | 9/2002 | Chen ..................... A01K 1/12 119/14.08 |
| 2016/0238620 A1* | 8/2016 | Shimamori .......... G01N 33/491 |

FOREIGN PATENT DOCUMENTS

| CN | 108226541 A | 6/2018 |
| WO | WO 02/069697 A1 | 9/2002 |
| WO | WO 2004/034063 A2 | 4/2004 |

OTHER PUBLICATIONS

International Search Report (PCT/ISA/210) issued in PCT/NL2019/050621 dated Feb. 20, 2020.
(Continued)

*Primary Examiner* — Christine T Mui
*Assistant Examiner* — Jonathan Bortoli
(74) *Attorney, Agent, or Firm* — Birch, Stewart, Kolasch & Birch, LLP

(57) ABSTRACT

A milking system includes a milking device, a milk line, and a sampling and analysis device for milk from the milk line, that includes a control unit, a carrier with reagent pads to detect a substance in the sample, a dosing device to dose a sample onto a reagent pad, an sensor device to detect radiation from that reagent pad, and to analyse the detected radiation to indicate a presence or concentration of said substance. The dosing device includes a nozzle with a supply line, a pump for pumping liquid to the nozzle, a flat wall part, and a mover to press the flat wall part and the nozzle against each other to close the nozzle. In this way, the nozzle can be filled completely to a known level and without bubbles. Thereafter, the sample pump can provide a sample droplet with known volume, which enables better control over the sample supply process.

20 Claims, 3 Drawing Sheets

(56) References Cited

OTHER PUBLICATIONS

Written Opinion (PCT/ISA/237) issued in PCT/NL2019/050621 dated Feb. 20, 2020.

* cited by examiner

MILKING SYSTEM WITH DETECTION SYSTEM

The present invention relates to a milking system, comprising a milking means for milking milk from a dairy animal, a milk line in fluid connection with the milking device, a sampling and analysis device arranged to take a sample of the milk from the milk line and to analyse milk from the sample, wherein the sampling and analysis device comprises a control unit for controlling the sampling and analysis device, a carrier comprising a base material with provided thereon one or more reagent pads, that are arranged to provide a detectable response in the presence of at least one substance in the sample, a dosing device arranged to provide, under the control of the control unit, a part of the sample onto one of the reagent pads, an optical sensor device arranged to detect optical radiation from said reagent pad supplied with said part of the sample, and to analyse the detected optical radiation to provide an indication of a presence or concentration of said at least one substance, wherein the dosing device comprises a nozzle with a supply line for supplying a portion of the milk sample to the nozzle, the nozzle being arranged for supplying the part of the sample to the reagent pad, and a pump that is controlled by the control unit and is arranged for pumping liquid through the supply line towards the nozzle.

Document WO02/069697A1 discloses a milk sampling and analysis apparatus for use in a milking system, and comprising a tape carrying dry sticks with reagents. When sampling, a few drops of a milk sample are dropped onto the dry stick, and excess fluid is collected in a funnel under the dry stick. the reaction of the sample on the dry stick is detected by means of a CCD camera.

A problem with the known device is that the supply control of the sample onto the reagent is not very well controlled. It requires relatively long stretches of reagent on the strip, as well as large flushing holes and a wide waste funnel. Since most reagents are or contain enzymes or other biological agents, that require a lot of resources to produce, it seems that the known device is not always very good a tsampling efficiently. In milking systems, in particular robotic milking systems that operate without human supervision, it is advantageous if they can operate for a long time without requiring human intervention. Therefore, it is desirable to have a large number of reagents available for sampling, which also requires efficient a sampling set-up.

It is therefore an object of the present invention to provide a milking system of the kind set out above, that is able to sample more efficiently, in particular allowing better control over the sampling procedure.

It is another object of the present invention to provide a milking system of the kind set out above, that is able to perform efficiently over a prolonged period without human intervention.

The present invention achieves at least one of these objects. Thereto, in a first aspect, the present invention provides a milking system according to claim 1, in particular a milking system, comprising a milking means for milking milk from a dairy animal, a milk line in fluid connection with the milking device, a sampling and analysis device arranged to take a sample of the milk from the milk line and to analyse milk from the sample, wherein the sampling and analysis device comprises a control unit for controlling the sampling and analysis device, a carrier comprising a base material with provided thereon one or more reagent pads, that are arranged to provide a detectable response in the presence of at least one substance in the sample, a dosing device arranged to provide, under the control of the control unit, a part of the sample onto one of the reagent pads, an optical sensor device arranged to detect optical radiation from said reagent pad supplied with said part of the sample, and to analyse the detected optical radiation to provide an indication of a presence or concentration of said at least one substance, wherein the dosing device comprises a nozzle with a supply line for supplying a portion of the milk sample to the nozzle, the nozzle being arranged for supplying the part of the sample to the reagent pad, a pump that is controlled by the control unit and is arranged for pumping liquid through the supply line towards the nozzle, a flat wall part, and a mover arranged to press the flat wall part and the nozzle against each other to thereby close the nozzle.

Herein, "close the nozzle" is understood to mean that by pressing the nozzle against the flat wall part, or vice versa, the nozzle is substantially closed off. However, it will be clear that, depending on the roughness of the nozzle exit and the flat wall surface, and the force with which both are pressed against each other, some leakage will be possible.

By means of the set-up described above, it is possible for the nozzle to be filled up to its rim with liquid, a well-defined meniscus being formed at its exit surface. This may be achieved e.g. by having the pump provide a surplus of liquid to the nozzle. This surplus can leave the exit between the nozzle surface and the flat wall part, because of the nozzle not being quite closed off sealingly. This surplus liquid may be ejected sidewardly. Importantly, the nozzle is now completely filled, without air remaining in the nozzle, nor there being a bulging droplet of unknown dimensions. By thus knowing exactly the geometry at the nozzle exit, the pump can deliver a very well controlled droplet to the reagent pad, and not more liquid than that. This has a number of advantages. First of all, it allows tight control of the area of the reagent pads, in that spilling of liquid to or onto a neighbouring reagent pad can be prevented efficiently. In addition, the tight control over the volume and dimensions enable to know exactly when the sample droplet will touch the reagent pad, thus when liquid will start to be transferred and when the reaction starts. Thus the reagent pads may be made smaller, thereby requiring less resources for producing same. It also ensures in some embodiments that a collection of a certain number of reagent pads takes up less space than before, or vice versa: a similar volume of reagent pads now contains a higher number thereof, so that the sampling and analysis device can operate for a longer time without human intervention, such as for changing a tape or cartridge. Another advantage is that the chance of there being excess liquid is smaller, so that there is less waste, but also less a smaller of spilling liquid in the device or its environment. This in turn improves the reliability and accuracy of the measurements, and requires less cleaning.

Particular embodiments of the invention, as well as features and advantages thereof, are described in the dependent claims, as well as in the now following part of the description.

In embodiments, the flat wall part comprises a flexible material, in particular an elastic membrane. By means of the flexible material, tolerances in the nozzle surface may be accounted for, such that the "sealing contact" is achieved for substantially every nozzle surface. This also allows excess liquid to escape more easily between nozzle surface and the flat wall part. In addition, because the flat wall part is flexible, the counterpressure or -force exerted on the liquid is relatively small, and well-defined. All this further helps in the formation of a well-defined meniscus. Herein, "flexible" means that the flat wall part may undergo a detectable elastic deformation under the influence of the pressure of the liquid from the nozzle. The wall part is preferably an elastic membrane, such as in particular a rubber membrane.

In embodiments, the dosing device further comprises a nozzle mover that is arranged to move the displaceable nozzle under the control of the control unit in a longitudinal direction, such as towards and away from the tape or the flat wall part. The nozzle mover is thus arranged to bring the nozzle to an object, and withdraw it therefrom. For example, if the nozzle is to be filled to the rim with liquid, it is first brought to the flat wall part, filled with liquid, and then withdrawn. Likewise, if the nozzle is to supply a sample of liquid to a reagent pad, it is brought towards the pad, releases a liquid sample, and is withdrawn. Important to note here is that withdrawing the nozzle may help in controlling and preventing excess liquid. Note that the total direction of movement may be more complex than simply in the longitudinal direction of the nozzle. E.g. the flat wall part and the tape are often in different positions, so that the nozzle is preferably moveable in a direction perpendicular to the longitudinal direction as well. Having such a nozzle mover thus increases the flexibility of the system.

In embodiments, the mover comprises a flat wall part mover, that is arranged to move the flat wall part between the nozzle and the carrier with the reagent pad. Instead of, or in addition to, having a nozzle that is moveable in a direction perpendicular to its longitudinal direction, it is, in these embodiments, the flat wall part that is moveable, in particular towards and in front of the nozzle. In this way the moveability of the nozzle may be limited to the longitudinal direction, which ensures a better, more reliable control over the movements. This in turn increases precision of sample delivery, and thus of the measurements and analysis. In use, the flat wall part is moved to the front of the nozzle. The nozzle and the flat wall part are brought into contact with each other, the nozzle is filled to the rim, and the flat wall part is retracted. Now the nozzle is ready for supplying a droplet of liquid to a reagent pad.

In embodiments, during provision of the part of the sample the reagent pad is facing downward. By means of this measure, gravity assists in the control of sample liquid supply, in that it does not exert an additional force on the liquid, but rather a counteracting force. This means that the chance of too much liquid being provided onto the reagent is much reduced. This in turn allows the use of a smaller reagent pad, as well as it reduces the chance of supplied liquid spilling over too a neighbouring reagent pad. Alternatively, just because that risk has been reduced, it is now possible to limit the measures that should prevent this spilling, such as a too great distance between the reagent pads or the like. In addition, in case there would still be provided too much liquid to the reagent pad, it is likely that this will be collected again by the sample supply system, since gravity would pull the liquid back into that direction.

Preferably, during provision of the part of the sample the reagent pad is facing away from the optical path to the optical sensor. This means that the reagent is provided on a first side of the tape, while the radiation from the reagent pad, that follows the optical path to the optical sensor, is emitted through the tape and emerges from the opposite side of the tape. In the simplest case, the sensor is provided directly above this opposite side of the tape. It is also possible to provide the optical sensor remotely, the optical radiation being guided to the optical sensor by means of optical device such as a mirror or a lightpipe. In such cases, the optical sensor need not physically face away from the reagent pad. However, the optical path is still through the tape and away from the reagent pad. An advantage of this set-up is that the development in time of the response of the reagent to the droplet of sample liquid can be followed more clearly, since the colouring or discolouring can be observed from below, i.e. a clear reagent pad, instead of from above, i.e. from an already coloured reagent pad. And if a drop of the sample liquid would fall off the reagent pad, it will not fall in the direction of the sensor (or any optical device in the optical path, but rather away from it, which will reduce the likelihood of such drops affecting measuring reliability and accuracy. Herein, the sensor is thus not positioned right below the reagent pad, but for example above the pad, and it looks through the tape onto the pad. Alternatively, the pad may be moved and turned, so that it extends in a vertical plane or the like, the sensor then being arranged horizontally, and so on.

In embodiments, the pump is arranged for sucking back liquid from the nozzle. This allows liquid to be supplied in a very controlled way, in that for example a liquid drop is supplied such that it makes contact with the reagent pad, and is subsequently sucked back in order to break the contact between the droplet and the reagent pad. This enables further control over the liquid supply, and this may prove advantageous in particular in the case of reagent pad/liquid combinations that show a relatively slow transfer speed and/or capillary action, so that there is a relatively long time for controlling this liquid transfer.

In embodiments, the sampling and analysis device further comprises a sealing rim arranged around the flat wall part, the sealing rim and the flat wall part together forming a first space for receiving the nozzle. This ensures that liquid that escapes between the flat wallpart and the nozzle, and thus moves more or less to the side, is not ejected into the space of the sampling and analysis device, but may now (also) be collected in the second space, and e.g. drained.

In embodiments, the dosing device comprises an overflow device comprising a wall at least partly surrounding the nozzle, an overflow space being provided between the wall and the nozzle, further comprising a discharge connected or connectable to the overflow space. This allows surplus liquid to be collected in the overflow device. This is not only advantageous for collecting inadvertent surplus liquid. in order to prevent droplets from soiling the apparatus. It further allows deliberate flushing of the nozzle with liquid, even in place, without such risk of soiling the apparatus. The sampling and analysis device may e.g. be arranged to supply a cleaning portion of the sample before supplying the part of the sample proper. To do this, the nozzle is first brought in a position relatively remote from the reagent pad. This prevents accidental transfer of liquid to the reagent pad. Subsequently, the control unit arranges the sampling and analysis device, such as a pump thereof, to supply a first part of the sample, here called a cleaning portion, to the nozzle. This cleaning portion exerts a cleaning action on the nozzle, removing older sample liquid and/or dirt that may have remained or collected there, respectively. This cleaning portion is collected in the overflow device, and carried of via the discharged. After the is cleaning action, the now clean nozzle may supply a part (droplet) of the sample for transfer to the reagent pad. If desired, The sampling and analysis device may alternatively or further be arranged to supply a separate cleaning fluid, such as water, optionally with a cleaning agent, to the nozzle. Again, this cleaning fluid may be collected in the overflow device, and drained via the discharge. In all these cases, it is advantageous that the supply of liquid, be it milk or other sample fluid, and/or cleaning fluid is against the direction of gravity, so that an optimum control over the flow of liquid may be exerted, and that cleaning may be performed without any further complications.

In embodiments, the wall of the overflow device and the sealing rim are in sealing contact when the nozzle is received in the first space, the first space and the overflow space being in direct fluid connection. This ensures that the draining of the ejected excess liquid may be via the drain of the overflow space, and prevents an undesirable counterpressure by the fluid to be drained.

In embodiments, the discharge has a cross-sectional discharge area that is at least twice as large, preferably four times as large, as a cross-sectional supply area of the supply line. This ensures that the discharge of the collected liquid/excess liquid is substantially always possible with a low pressure/low vacuum, which helps in preventing draining problems, as well as prevents counterpressure on the liquid in the nozzle.

In embodiments, the carrier comprises a tape wound on a tape reel carrying the tape, said tape comprising a base material with provided thereon a series of said reagent pads, wherein the sampling and analysis device comprises a tape mover, arranged to move and unwind, under the control of the control device, said tape. Although it is possible to provide dry sticks with one or more reagent pads, as in the system known from document WO02/069697A1, it is advantageous if the reagent pads are provided all on a tape. Tape control constructions are well-known in the art, and rather simple and reliable, and e.g. resemble a tape deck. This allows to have up to thousands of reagent pads on one tape, and a very long uninterrupted operating time.

Importantly, many of the above described advantages are not limited to the use of the sampling and analysis device in a milking system. Rather, the ability to better control delivery or supply of a part of a sample to a reagent using a flat wall part and a nozzle may be used in substantially any liquid sampling and analysis system. Therefore, the present invention also provides a sampling and analysis device comprising a control unit for controlling the sampling and analysis device, a carrier comprising a base material with provided thereon one or more reagent pads, that are arranged to provide a detectable response in the presence of at least one substance in the sample, a dosing device arranged to provide, under the control of the control unit, a part of the sample onto one of the reagent pads, an optical sensor device arranged to detect optical radiation from said reagent pad supplied with said part of the sample, and to analyse the detected optical radiation to provide an indication of a presence or concentration of said at least one substance, wherein the dosing device comprises a nozzle with a supply line for supplying a portion of the milk sample to the nozzle, the nozzle being arranged for supplying the part of the sample to the reagent pad, a pump that is controlled by the control unit and is arranged for pumping liquid through the supply line towards the nozzle, a flat wall part, and a mover arranged to press the flat wall part and the nozzle against each other to thereby close the nozzle. It is expressly noted that all the features of all dependent claims as well as of all embodiments described for the milking system according to the invention are also applicable to the sampling and analysis device, with corresponding advantages.

The invention will now be explained further by means of a number of embodiments described below and in the drawings, in which:

FIGS. 4a-c show prior art filling of a nozzle, while

Figure 1:
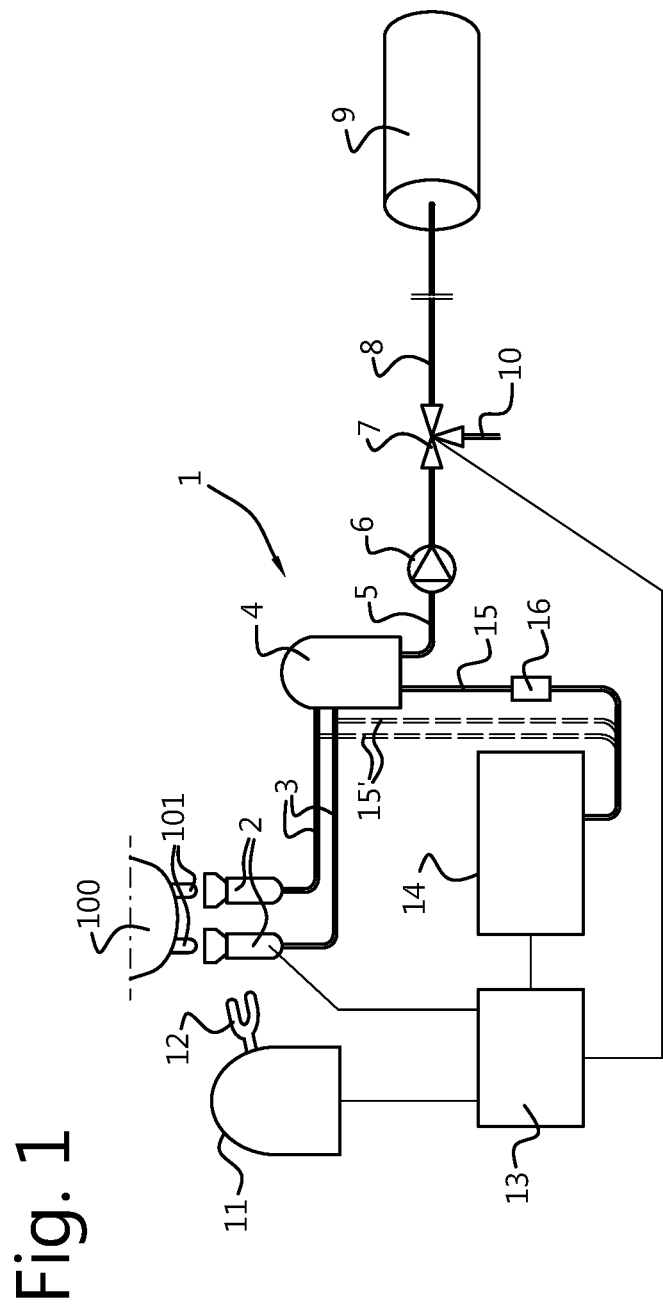
FIG. 1 shows a diagrammatic representation of a milking system according to the present invention.

FIG. 1 shows a diagrammatic representation of a milking system 1 according to the present invention for milking teats 101 of an udder 100 of a dairy animal. The milking system 1 comprises teat cups 2, connected to short milk lines 3, debouching in a milk jar 4, that in turn is connected to a main milk line 5. A milk pump is denoted 6, and a three-way valve with 7 connects to a bulk tank line 8 connected to a bulk milk tank 9, and to a sewer line 10.

A milking robot 11 has a robot arm 12 and a robot control unit 13. A sampling unit is generally denoted 14, and a sampling line 15 with an optional sample valve 16.

In use of the milking system 1, the robot control unit 13 controls the milking robot 11 with the robot arm 12 to attach the teat cups 2 to the teats 101 of the udder 100 of a dairy animal such as a cow. The milk that is subsequently milked leaves the teat cups 2 under the influence of a vacuum, that is applied by a pump not depicted here, via the short milk lines 3, and is collected in a milk jar 4.

In order to comply with legal requirements, the first milk from each teat must be tested for physical changes, and if desired for other deviant properties. This can be done by means of a separate foremilk test device, or it can be done with the help of the sampling unit 14 as supplied according to the invention. Then use will be made of the alternative sample lines 15'. In case of a negative assessment, the milked milk collected in the milk jar 4 will then be pumped to the sewer line 10 by means of the milk pump 6, via the main milk line 5 and the three way valve 7. All these devices are under the control of the robot control unit 13. Contrarily, if the milk is assessed to be OK, it will be pumped to the bulk milk tank 9 via the bulk line 8.

It is also possible that the sampling unit 14 takes a sample from the milk jar 4, in particular a mixed sample from milk that was milked from all teats and during all of the milking. This helps to get a good assessment of the milk that (if not rejected based on the foremilk assessment or otherwise, such as being antibiotics milk) will be sent to the bulk tank 9, or possible to one of several bulk milk tanks. For example, the milk from different cows could be sent to different bulk tanks, based on their fat content, their protein content or otherwise, as determined by the sampling unit 14. In such embodiments, as the one shown in FIG. 1, the sample line 15 runs from the milk jar 4 to the sampling unit 14, and optionally has a sample valve 15. Note that the latter could also be a part internal to the sampling unit 14.

Most often, however, the sampling unit 14 is used to determine a property of the milk from a cow, either per teat quarter 101 or for the whole udder 100/animal, which property is subsequently used in animal management but not for immediate control of the milk destiny. Examples are the measurement of hormones such as progesterone, that play a role in the reproductive cycle of the animal, or of substances that relate to feeding or metabolic health of the animal. Based on the assessment by the sampling unit 14, the farmer or the control unit 13 may then adapt feeding, call a veterinary for a health check or for insemination, and so on.

Figure 2:
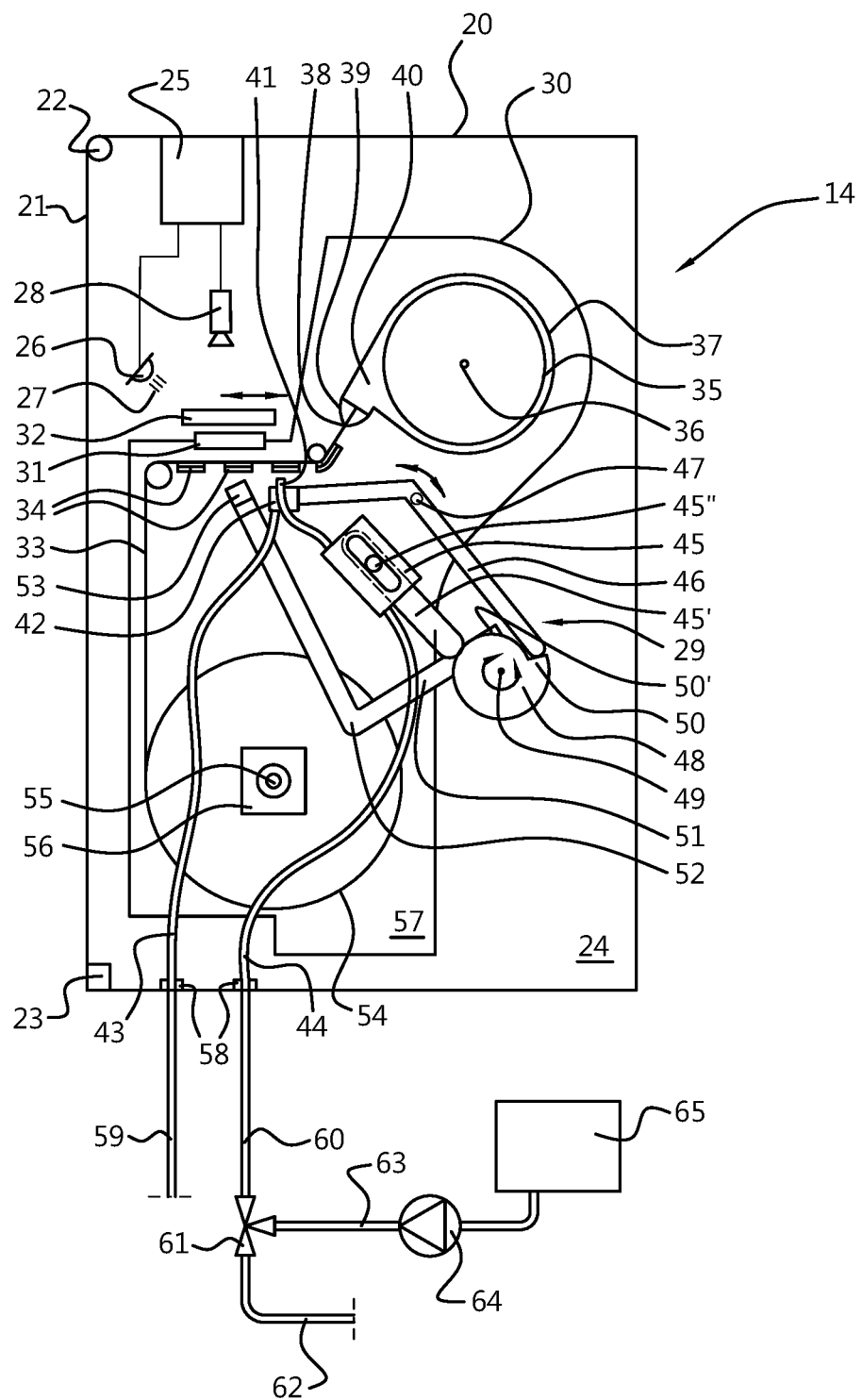
FIG. 2 shows a diagrammatic representation of a sampling unit as in the milking system according to the present invention.

FIG. 2 shows a diagrammatic representation of a sampling unit 14 as in the milking system according to the present invention. The sampling unit 14 has a box 20 with a lid 21 that hinges around a hinge 22 and is locked with a lock 23, and with an in-box space 24. In the box 20 there are provided a sampler control unit 25, a light source 26 emitting light 27, a camera 28, a drive 29 and a cassette 30.

The cassette 30 has a window 31, that can be covered with a shutter 32, and through which a tape 33 with reagent pads 34 may be observed. The tape 33 is wound from a supply reel 35, rotatable around an axle 36 in a subhousing 37, that has an exit opening 38 closed by means of a seal 39 and that surrounds an internal subhousing space 40. A nozzle is denoted by 41, is partly surrounded by an overflow cup 42 with a housing drain line 43, and is itself connected to a housing supply line 44, which is controlled by a sample pump 45.

The drive 29 comprises a nozzle mover arm 46, which is hingeably driveable around a hinge 47 by a first cam wheel 48, which in turn is rotatably driven around an axle 49 by non-shown cam wheel drive and which has a first cam 50. The drive 29 also comprises a pump drive arm 45', which drives a moveable pump element 45". The drive 29 also comprises an rinsing cup mover arm 51 that is driveable around a hinge 52 by a second cam 50', and that at its end carries a rinsing cup 53.

The used tape is collected around a collecting reel 54 that is driveable around an axle 55 by means of a tape drive 56. The inner housing space is denoted by 57. Liquid connectors 58 supply connections for an external drain line 59 and an external supply line 60, the latter being connectible, via valve device 61, to a milk sampling line 62, such as the sampling line 15 of FIG. 1, as well as a cleaning fluid supply line 63, that supplies cleaning fluid via a supply pump 64 from a reservoir 65.

The sampling unit 14 as shown here comprises a substantially light- and airtight box 20, with a number of fixed parts and a replaceable cassette, or housing, 30 with a relatively large number of parts that are replaced each time the cassette 30 is replaced. However, it is e.g. also possible to limit the replacement to the supply reel 35 with the tape 33 with the reagent pads 34. This will be shown later on.

In the embodiment of FIG. 2, the cassette or housing 30 may be exchanged by unlocking the lock 23, such as by turning a key, shifting a bolt or the like, subsequently opening the lid 21 around the hinge 22, taking out the used cassette 30 and replacing it with a new and unused cassette. The fluid connections 58 between housing drain line 43 and the external drain line 59, and between the housing supply line 44 and the external supply line 60, respectively are made, either manually or automatically by placing the cassette 30. The various arms 45', 46, 51 driveable by the drive 29 are in an idle position in which they come to rest against respective cams, two of which are shown here as the first and second cams 50, 50', respectively. Thereafter the sampling unit 14 is closed again. It is noted that other means of moving the nozzle and/or the rinsing cup, instead of the mover arms 45', 46 and 51 may be used, such as pneumatic means, that can be connected via gas tubes and fluid connectors, connectible like the drain and supply lines, and controllable via gas pumps, or any other suitable means.

In use, a sample of milk is supplied through the milk sampling line 62, such as from the milk jar 4 in FIG. 1, and via the valve device 61 and the external supply line 60, a fluid connector 58, the housing supply line 44 the sample pump 45 and the nozzle 41. Thereto, the sample pump is put in an open position by means of the moveable pump element 45", driven by the pump drive arm 45' under the control of the drive 29, in turn controlled by the sampler control unit 25. It is noted that the sampler control unit is a part inside the box 20, and separate from the robot control unit 13 in FIG. 1. It is also possible that the sampler control unit is provided outside the box 20, still as a separate part, or even as an integral part of the robot control unit 13. It is furthermore noted that, according to the invention, use will be made of a flat wall part, as provided in the rinsing cup 53, but this will be elucidated in relation to FIG. 3 and further. The sample pump 45 may be any suitable pump such as a peristaltic pump. The latter has an advantage in that it is easily closable, such as by pressing the moveable pump element against an abutment surface, and is accurately controllable for dosing small amounts, such as a droplet of sample onto a reagent pad. Nevertheless, other types of pumps that can provide good dosing control are not excluded.

A droplet of the sample is thus provided by the nozzle 41 on a reagent pad 34. These reagent pads 34 are provided as a series of consecutive pads on a tape 33, and provide a detectable response in the presence of a (detectable) amount of to-be-detected substance in the milk sample. For example, the reagent pad 34 may show a colouring in the presence of progesterone in the milk sample, the intensity of speed of the colouring depending on the concentration of the progesterone. of course, other substances may also be used. The response, or absence thereof, is detected by means of a camera 28 that images, through a window 31 in the box, radiation coming from the reagent pads 34. This radiation is either radiation 27 that was emitted by the light source 26, and then reflected or scattered by the reagent pad 34, or may be radiation of a different type, generated by a reaction in the reagent to the radiation 27 from the light source 26, such as a fluorescence reaction. The light source 26 may emit optical radiation, such as visible light, UV(A) radiation or (near) infrared light, and is selected suitable, such as from corresponding LEDs or other. The window may optionally be covered by means of a shutter 32 that is movable in the direction of the double arrow, in order to protect the contents of the cassette 30, and in particular the tape 33 with the reagent pads 34, against any negative influences of the radiation.

After the nozzle 41 supplies a droplet of the milk sample to a reagent pad 34, the camera 28 observes the pad, and detects any response. Thereto, the pad 34 is first moved by means of the tape mover 56 that advances the tape 33 a bit. This not only frees up a subsequent pad 34, but also moves the pad to the field of view of the camera 28. Note that it is also possible that that field of view is where the sample droplet is provided by the nozzle 41. That allows to observe the response in the reagent pad immediately. Also, the new unused pad can stay in a protected environment for as long as possible. Preferably, the field of view of the camera 28 contains more than one reagent pad 34. This allows a reagent pad to stay in view for more than the average milking/sampling time. For dairy cows and sampling every cow, this time may be as short as a few minutes. Such a short time requires a relatively high dose of reagent in the reagent pads. This is not necessary if the reagent pad stays in view for a longer time, such as double or triple the time, which can be achieved by having two or three reagent pads in view of the camera 28. Of course, other numbers are possible as well, although very high numbers reduce the amount of visual information that the camera 28 may extract from each individual reagent pad 34.

After assessment by the camera 28, the tape 33 with the now used reagent pads is pulled further forward by the tape mover 56, and is eventually rolled onto the collecting reel

54. The tape mover 56 may be any kind of motor for turning the collecting reel 54, such as a motor from a cassette deck, or a stepper motor.

A tape 33 may comprise more than one type of reagent pad 34. The reagents for such reactions are often enzymes or other biologically active substances. Very often, these are quite sensitive to moisture, that can affect their properties. For example, moisture alone may lead to a colour reaction, which is of course undesirable because it is meaningless. It may also lead to a different sensitivity of the reagent, which deteriorates the accuracy of the measurement. For these and other reasons, it is advantageous that the presence of moisture is prevented and suppressed as much as possible.

The present invention suppresses moisture by a number of possible measures. First of all, and obviously, the box 20 is made as airtight as possible, so that moisture may in principle only be provided by air in the in-box space 24, the volume of which can be kept small. It is furthermore possible to provide moisture absorption inside the box 20, such as by means of an absorptive lining or by means of packages of absorbers such as silica gel or the like. However, because the box 20 is in principle a permanent part of the sampling unit of the milking system, such liners will inevitable become moisture saturated and thus ineffective, while the same holds for the absorber packages, that in the end will need replacement, which represents an undesirable human intervention if it can be prevented.

The cassette 30 in which the tape is provided need never have a higher (relative) humidity than the in-box space 24. Nevertheless, some moisture may seep through the box wall, because there will always be connections, either permanent or temporary. But more importantly, sampling inherently brings moisture into the cassette 30. Thus, measures to suppress moisture inside the cassette 30 are desirable as well. Thereto, for example, the supply reel 35 with the part of the tape 33 with unused reagent pads 34 is provided in a subhousing 37. The tape 32 exits the subhousing via an exit opening 38 that is sealed by means of e.g. a duckbill seal 39 or other suitable seal. This ensures that moisture from the inner housing space 57 will only very slowly enter the internal subhousing space 40. Since the tape 33 with the reagent pads 34 can, and will, be produced in a very dry environment, the air in the subhousing 37 can have an extremely low (relative) humidity of, say, only a few %. Depending on the quality of the duckbill, the low humidity need rise only very slowly.

In order to further suppress moisture, the supply reel 35 itself is provided, according to the invention, at least at its surface with a desiccant. In the presently shown example, the supply reel 35 is substantially made of a material with desiccant properties, which means that it is able to actively remove water from the surrounding air. This further ensures that the humidity inside the subhousing 37, thus at the unused reagent pads 34, remains at a suitable level, such as a few %, for an even longer time. And since the supply reel 35 may take up a substantial volume within the subhousing 37, depending on the ratio between the fully wound tape and the diameter of the supply reel 35, the total moisture absorption capacity may be very high.

The moisture absorption properties depend on the material used. Preferably, the material is a compound material, comprising at least a true desiccant/moisture absorber/adsorber, and a matrix to provide sufficient strength to the supply reel 35. A useful example is marketed by the company Capitol Specialty Plastics, Inc., for example for its Active-Vial™ M3003 series. Such materials comprise a physical desiccant, in which moisture is collected in microscopic pores (microsieve), surrounded by a polymer matrix, such as from polypropylene, polyethylene, mixtures thereof, and so on. To this is added a so-called channeling agent, such as EVOH (ethylene-vinyl alcohol), that ensures that channels are formed during (actually: after) mixing of the desiccant material and the (molten) polymer. These channels ensure that moisture can reach the desiccant material that was embedded in the polymer matrix. Thus, even deep-lying desiccant material can attract and bind moisture from the air, which greatly enhances the total absorption capacity. Yet, it is also possible to have the (true) desiccant material mainly at the surface of the supply reel 35. For example, in cases where the supply reel 35 is used for a relatively short time only, it may be better to have a high speed of absorption, with less total absorption capacity.

Yet a further optional measure is to have the collecting reel 54 also comprise desiccant material at least at its surface. Optionally, the collecting reel 54 is also substantially made of desiccant material, in much the same way as described above for the supply reel 35. the advantages are manifold, e.g. in that all moisture in the air in the the inner housing space 57, in particular from supplied samples that escapes to the inner housing space 57, may be absorbed by the collecting reel 54. This helps reduce the humidity in said space, which in turn limits the seeping of moisture to the subhousing 37. Note that providing such a subhousing 37 is not necessary, although advantageous, especially if the collecting reel 54 is also provided with, or from, desiccant material, since then there is a very large moisture absorption capacity and/or speed from both reels 35 and 54.

The advantages of the present invention, relating to the use of a flat wall part in forming a sample droplet, will now be explained further in connection with FIG. 3 and in particular 4*d*. However, the starting point is FIG. 2, that shows in particular the rinsing cup mover arm 51 with the rinsing cup 53, the nozzle mover arm 46 with the nozzle 41, and the drive 29. The rinsing cup 53 comprises a flat wall part against which the nozzle 41 will be pressed during preparation of the sample droplet formation. Thereto, the drive 29 is operated to rotate the nozzle mover arm 46 around the hinge 47 and/or the rinsing cup mover arm 51 around the hinge 52 such that the nozzle 41 is pressed against the (bottom of the) rinsing cup 53. Then the drive 29 is operated further to allow the sample pump 45 to fill the nozzle 41 with sample liquid, after which the nozzle is retracted from the rinsing cup, the latter subsequently being swung away by further operating the drive 29. The nozzle 41 is then ready to be brought to the reagent pad 34 by again operating the cam wheel of the drive 29, and to supply the reagent pad with a droplet of the sample liquid, as metered by the suitably controlled sample pump 45.

Figure 3:
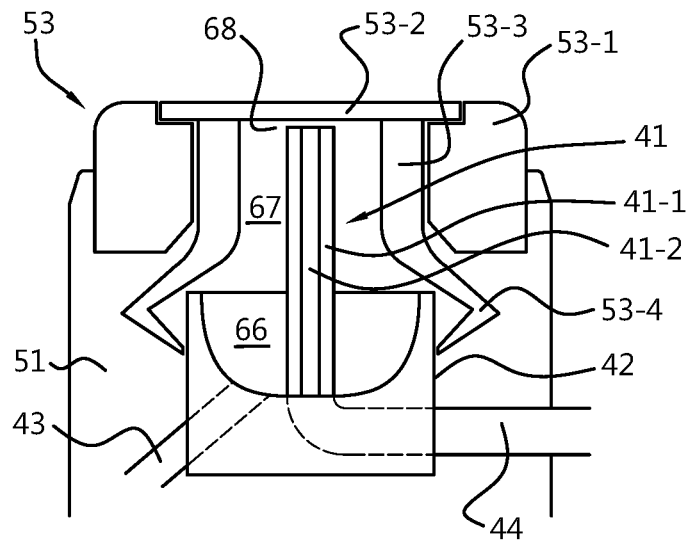
FIG. 3 shows a detail of an embodiment of the invention at sample droplet preparation.

In more detail, FIG. 3 shows the overflow cup 42 with the nozzle 41, comprising a nozzle wall 41-1 and a nozzle channel 41-2, and with the housing drain line 43 and the housing supply line 44. An overflow space is denoted by 66. Furthermore, a distal end of the rinsing cup mover arm 51 carries the rinsing cup generally denoted 53, comprising a cup wall part 53-1, a flat bottom 53-2, a bellows base part 53-3 and a bellows 53-4. A rinsing space is denoted by 67. The nozzle mover arm 46 of FIG. 2 has not been shown here to prevent obfuscation of relevant details. A slit 68 is present between the top of the nozzle 41 and the flat bottom 53-2.

It is remarked that here the rinsing cup 53 is built up in different parts 53-1 through 53-4, which allows to optimise each part for its specific function. It is however likewise possible to form the rinsing cup 53 as a unitary part, such as by injection moulding or the like.

In use, for preparation, the overflow cup 42 with nozzle 41 is first positioned inside the rinsing cup 53, by suitably operating the drive 29 to move the respective mover arms 46 and/or 51. Herein, the bellows 53-3/53-4 of the rinsing cup 53 helps to position and center the nozzle, and at the same time seal off the nozzle against the environment. In such a way, a sealed off volume is formed, from the combined overflow space 66 and the rinsing space 67. Note that these will overlap and, due to the nature of the flexible bellows, can have a varying volume. The tip of the nozzle 41 will come to rest against the flat bottom 53-2 of the rinsing cup, which will in principle seal the nozzle channel 41-2. However, the flat bottom 53-2 is made of a somewhat flexible material, such as a rubber membrane. Then, when liquid is supplied to the nozzle channel 41-2, a narrow slit 68 will be formed. When liquid is now ejected by the nozzle, this liquid will be collected in the overflow space 66 of the overflow cup 42, and will then be drained off via the housing drain 43. Such liquid may be rinsing liquid, such as hot, tepid or cold water, if desired with one or more cleaning agents, e.g. from a milking robot cleaning operation. It may also be milk, such as the first milk from a new sample, in order to flush away possible residues of a previous sample. Importantly, the nozzle channel will not only be freed from previous milk sample residues, but also from any remaining air bubbles, such that the nozzle channel will be completely filled. When thus flushing the nozzle 41, the flushing liquid is drained via the housing drain line 43. Note that this line has a larger cross-sectional are than the housing supply line, in particular at least 2-4 times as large, in order to prevent the build-up of liquid in the spaces 66, 67, and thus to prevent a counterpressure against the supply of liquid through the nozzle channel 41-2.

A further advantage of the flat bottom is that the amount of liquid in a drop can be controlled very well. This will now be elucidated in respect of FIG. 4a-d.

Figure 4A:
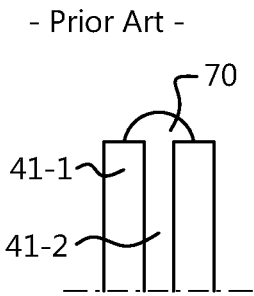
Figure 4B:
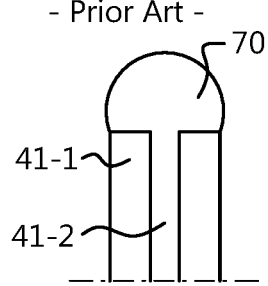
Figure 4C:
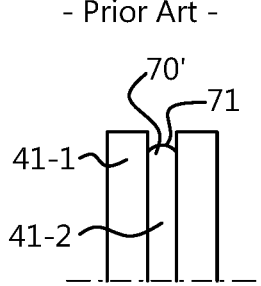
Figure 4D:
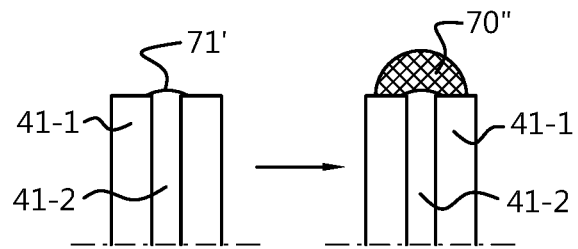
FIG. 4d shows filling of the nozzle in an embodiment of the invention.

FIGS. 4a-c show three possible degrees of filling a prior art nozzle channel 41-2. In FIG. 4a, there is an average filling, with some bulging of a droplet 70 over the nozzle wall 41-1 and tip. In FIG. 4b, there is a near-maximum filling, with a heavily bulging droplet 70. FIG. 4c shows a case where the channel 41-2 is incompletely filled with liquid 70' with a convex meniscus 71. When the channel 41-2 would have been filled with a liquid with a convex meniscus, it might e.g. have filled the channel only near the channel wall, while in the centre of the channel, the liquid level would have been lower than the tip, but here, too, there will be at least some air below the level of the tip of the nozzle. In short, there may be many possible filling levels of the nozzle 41. However, this is disadvantageous when trying to supply a known amount of fluid in the sample droplet.

To correct this, according to the invention, as has been shown in FIG. 3, the channel 41-2 is completely filled, but not more than that, by ejecting fluid with the nozzle pressed against a flat bottom. What then remains is shown in the left part of FIG. 4d: a completely filled nozzle channel 41-2 with a very low, but importantly a known meniscus 71'. Thereafter, a non-shown sample metering device such as a peristaltic pump, meters a known amount of sample fluid into the housing supply line, with the result shown in the right part of FIG. 4d: a sample droplet 70" of a known and constant volume. The added volume has been indicated as the crosshatched volume. But the important thing is that the droplet has known dimensions. This prevents undesired (premature or otherwise) falling off of a too big droplet. It also ensures that when the droplet is brought towards the reagent pad, it will be known exactly when the droplet touches the reagent pad, and thus the moment when the reaction will begin. It moreover prevents an incorrect reaction in the reagent pad due to a lack of liquid in the sample droplet.

It is noted that the droplet may be of a volume that is larger than is required by a specific reaction or reagent pad size. It is then possible to suck away the surplus liquid by reversing the sample pump or the like. This may be done after a predetermined time or according to some other measure. It is noted that this will work best when the sample is supplied from below, since then gravity will not interfere with the sucking back of the sample droplet. Yet, it is not excluded to implement the sucking back feature in other embodiments, such as where the sample is supplied from above.

It is remarked here that in the embodiments shown, in particular the one in FIG. 2, a number of parts is optional, or may be replaced by alternatives. In particular, but not exclusively, the cassette or housing 30 and/or the subhousing 37 may be dispensed with. The window 31 may then also be dispensed with, such that the camera 28 looks directly onto the reagent pads 34. The camera 28 and/or the light source 26 may also be provided outside the box 20, and so on, and so on. all such alternatives should not distract from the gist of the present invention, as already worded above, and that relates to a better control of the sample liquid supply, and that uses a flat wall part against which the nozzle is pressed before actually supplying the droplet. Herein, it is noted that when (many) more than one droplet is supplied, the relative importance of the invention becomes less.

The above described embodiments only serve to help explain the invention without limiting this in any way. The scope of the invention is rather determined by the appended claims.

The invention claimed is:

1. A milking system, comprising a milking device for milking milk from a dairy animal, a milk line in fluid connection with the milking device, and a sampling and analysis device arranged to take a sample of the milk from the milk line and to analyse milk from the sample, wherein the sampling and analysis device comprises:
   a control unit for controlling the sampling and analysis device;
   a carrier comprising a base material with provided thereon one or more reagent pads, that are arranged to provide a detectable response in the presence of at least one substance in the sample;
   a dosing device arranged to provide, under the control of the control unit, a part of the sample onto one of the reagent pads; and
   an optical sensor device arranged to detect optical radiation from said reagent pad supplied with said part of the sample, and to analyse the detected optical radiation to provide an indication of a presence or concentration of said at least one substance,
   wherein the dosing device comprises:
      a nozzle with a supply line for supplying a portion of the milk sample to the nozzle, the nozzle being arranged for supplying the part of the sample to the reagent pad;
      a pump controlled by the control unit and arranged for pumping liquid through the supply line towards the nozzle;
      a flat wall part; and
      a mover arranged to press the flat wall part and the nozzle against each other to thereby close the nozzle.

2. The milking system according to claim 1, wherein the flat wall part comprises a flexible material.

3. The milking system according to claim 1, wherein the mover comprises a nozzle mover arranged to move the displaceable nozzle under the control of the control unit in a longitudinal direction.

4. The milking system according to claim 1, wherein the mover comprises a flat wall part mover arranged to move the flat wall part between the nozzle and the carrier with the reagent pad.

5. The milking system according to claim 1, wherein during provision of the part of the sample the reagent pad is facing downward.

6. The milking system according to claim 1, wherein the pump is arranged for sucking back liquid from the nozzle.

7. The milking system according to claim 1, comprising a sealing rim arranged around the flat wall part, the sealing rim and the flat wall part together forming a first space for receiving the nozzle.

8. The milking system according claim 1, wherein the dosing device comprises an overflow device comprising a wall at least partly surrounding the nozzle, an overflow space being provided between the wall and the nozzle, further comprising a discharge connectable to the overflow space.

9. The milking system according to claim 7, wherein the dosing device comprises an overflow device comprising a wall at least partly surrounding the nozzle, an overflow space being provided between the wall and the nozzle, further comprising a discharge connectable to the overflow space and wherein, when the nozzle is received in the first space, the wall of the overflow device and the sealing rim are in sealing contact, the first space and the overflow space being in direct fluid connection.

10. The milking system according to claim 8, wherein the discharge has a cross-sectional discharge area that is at least twice as large as a cross-sectional supply area of the supply line.

11. The milking system according to claim 1, wherein the carrier comprises a tape wound on a tape reel carrying the tape, said tape comprising a base material with provided thereon a series of said reagent pads, and wherein the sampling and analysis device comprises a tape mover arranged to move and unwind said tape, wherein the tape mover is under the control of the control device.

12. The milking system according to claim 1, wherein the flat wall part comprises an elastic membrane.

13. The milking system according to claim 11, wherein the dosing device further comprises a nozzle mover arranged to move the displaceable nozzle under the control of the control unit in a longitudinal direction towards and away from the tape or the flat wall part direction.

14. The milking system according to claim 1, wherein during provision of the part of the sample the reagent pad is facing downward, and away from the optical path to the optical sensor.

15. The milking system according to claim 2, wherein the dosing device further comprises a nozzle mover arranged to move the displaceable nozzle under the control of the control unit in a longitudinal direction.

16. The milking system according to claim 2, wherein during provision of the part of the sample the reagent pad is facing downward.

17. The milking system according to claim 3, wherein during provision of the part of the sample the reagent pad is facing downward.

18. The milking system according to claim 4, wherein during provision of the part of the sample the reagent pad is facing downward.

19. The milking system according to claim 2, wherein the pump is arranged for sucking back liquid from the nozzle.

20. The milking system according to claim 3, wherein the pump is arranged for sucking back liquid from the nozzle.

* * * * *